(12) United States Patent
Marashdeh et al.

(10) Patent No.: US 9,535,026 B2
(45) Date of Patent: Jan. 3, 2017

(54) ELECTRICAL CAPACITANCE VOLUME TOMOGRAPHY SENSOR FOR INSPECTION OF POST-TENSIONED TENDONS

(71) Applicants: Tech4Imaging LLC, Columbus, OH (US); Infrastructure Preservation Corporation, Clearwater, FL (US)

(72) Inventors: Qussai Marashdeh, Columbus, OH (US); Yousef Alghothani, Columbus, OH (US); Geoffrey Legg, Tewksbury, MA (US); Bill Seavey, Clearwater, FL (US); Bradley Hunter, Burlington, MA (US)

(73) Assignees: Tech4Imaging LLC, Columbus, OH (US); Infrastructure Preservation Corporation, Clearwater, FL (US)

( * ) Notice: Subject to any disclaimer, the term of this patent is extended or adjusted under 35 U.S.C. 154(b) by 176 days.

(21) Appl. No.: 14/564,204

(22) Filed: Dec. 9, 2014

(65) Prior Publication Data

US 2016/0161436 A1    Jun. 9, 2016

(51) Int. Cl.
*G01N 27/24* (2006.01)
*G01R 27/26* (2006.01)
*G01N 27/22* (2006.01)

(52) U.S. Cl.
CPC ............ *G01N 27/24* (2013.01); *G01N 27/226* (2013.01); *G01R 27/2617* (2013.01)

(58) Field of Classification Search
CPC ............................ G01N 27/24; G01R 27/2617
USPC .................................................. 345/419–427
See application file for complete search history.

(56) References Cited

U.S. PATENT DOCUMENTS

| | | | | |
|---|---|---|---|---|
| 4,737,621 A * | 4/1988 | Gonsiorowski | ........ | G02B 26/06 250/201.9 |
| 8,614,707 B2 | 12/2013 | Warsito | | |
| 2009/0222221 A1* | 9/2009 | Buyukozturk | ............ | G01S 7/41 702/35 |
| 2010/0033186 A1* | 2/2010 | Overweg | ............... | A61B 5/055 324/318 |
| 2011/0068773 A1* | 3/2011 | Harkness | ............. | G01R 15/186 324/127 |
| 2013/0085365 A1 | 4/2013 | Marashdeh | | |
| 2015/0210111 A1* | 7/2015 | Lin | ......................... | B60B 21/08 301/95.103 |

FOREIGN PATENT DOCUMENTS

JP          2013245496      * 12/2013  ............. E01D 11/02

\* cited by examiner

*Primary Examiner* — Jeff Natalini
(74) *Attorney, Agent, or Firm* — Standley Law Group LLP (57) ABSTRACT

The present invention provides a system and apparatus for inspecting tendons and cable stays in bridges and structures using multi-frequency excitation of an ECVT sensor.

19 Claims, 12 Drawing Sheets

Dielectric Constants of Fe2O3 Samples per Hiremath and Venkataraman, 2002

Figure 10
Roller Retracted

Figure 11
Roller in 5.5 Inch
Diameter Position

Figure 12
Roller in 4.5 Inch
Diameter Position

ELECTRICAL CAPACITANCE VOLUME TOMOGRAPHY SENSOR FOR INSPECTION OF POST-TENSIONED TENDONS

BACKGROUND AND SUMMARY OF THE INVENTIVE FIELD

Electrical Capacitance Tomography (ECT) is the reconstruction of material concentrations of dielectric physical properties in the imaging domain by inversion of capacitance data from a capacitance sensor.

Electrical Capacitance Volume capacitance imaging or ECVT is the direct 3D reconstruction of volume concentration or physical properties in the imaging domain utilizing 3D features in the ECVT sensor design. ECVT technology is described in U.S. Pat. No. 8,614,707 to Warsito et al. which is hereby incorporated by reference.

Adaptive Electrical Capacitance Volume Tomography (AECVT) provides higher resolution volume imaging of capacitance sensors based on different levels of activation levels on sensor plate segments. AECVT is described in U.S. Patent Application Publication US2013/0085365 A1 to Marashdeh et al. which is hereby incorporated by reference.

Post-tensioning is a method of reinforcing concrete, or other materials, with high strength steel strands or bars. Post-tensioning tendons are assemblies comprised of an outside sheathing or duct, the strands or bars, and any grout or other coating surrounding the strands or bars. Post-tensioned tendons systems are often used to reinforce segmental concrete structures and provide load bearing capacity. The tendons are typically anchored, stressed, and pumped with grout. The tendon forms a continuous bond along its length with the grout surrounding it. The bond is achieved through a cementitious matrix which surrounds the steel strands. The matrix acts with the polymer cylindrical container (duct) which encases the concrete member to complete the bond path between the prestressed strands and the grout member. When the grout hardens, through its bond to the steel strands, it locks the movement of the strands within the tendon to that of the grout surrounding it. Hence, the force in a bonded tendon becomes a function of the deformation of the concrete surrounding it. Long term reliability of the tendon requires continuous grout and bonding throughout the tendon. Discontinuities like air pockets (e.g., voids), un-cured grout (e.g., water), and partially-cured grout (e.g., bleeding grout) along the tendon weaken the tendon's ability to maintain its load and may eventually result in failure of the tendon. Discontinuities within the tendon's grouting system can lead to section loss (e.g., corrosion of the steel), broken wires and cables, undermining the integrity of a tendon system.

To assure tendon structural integrity, tendons must be inspected after grouting and periodically throughout the life of the structure. This requires an imaging technology that is able to make three-dimensional images of the inside of the tendon, to detect air, water, and bleeding grout pockets, to estimate volume of detected pockets, and to identify their location. The technology must be economical to employ and capable of producing acceptable images of discontinuities. Ideally, it should not use radiation that would require shielding to protect the operator and the users of the structure. Electrical Capacitance Volume Tomography (ECVT) satisfies these criteria. It's features include safety, high imaging speeds, light weight sensor design, and higher resolution imaging with use of AECVT sensors.

The present invention provides an innovative ECVT sensor and supporting features for inspecting tendons and cable stays in bridges and structures. The present invention can also be used to image other similar construction-type structures such as pipelines. It also provides a method for using ECVT sensor results for locating discontinuities in structures and rusted steel, and estimating their volume and location. The preferred embodiment of the present invention also involves an innovative design for the construction of an ECVT sensor that has the ability to travel along the length of a tendon using wireless control. The developed ECVT sensor preferably surrounds, or substantial surrounds, the tendon in order to make three-dimensional images and is adapted to open up easily for mounting and dismounting. In the preferred embodiment, it has modular design and can be fitted with a traction (movement) module to make it capable of autonomous travel. The design is scalable to accommodate larger and smaller tendons. It preferably incorporates a suspension mechanism that accommodates a specified range of tendon diameters. It also preferably employs a position tracking mechanism based on counting rotations of tractor wheels.

The present invention also provides an AECVT design using capacitance plates having a plurality of individually addressable segments with variable voltage distribution for detection of steel degradation using multi-frequency excitation. The integrative and adaptive data acquisition method is used to activate the ECVT sensor plates with different frequencies for detection and volume identification of rusted steel or broken steel cable strands.

BRIEF DESCRIPTION OF THE DRAWINGS

The following detailed description of the example embodiments refers to the accompanying figures that form a part thereof. The detailed description provides explanations by way of exemplary embodiments. It is to be understood that other embodiments may be used having mechanical and electrical changes that incorporate the scope of the present invention without departing from the spirit of the invention.

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Figure 1:
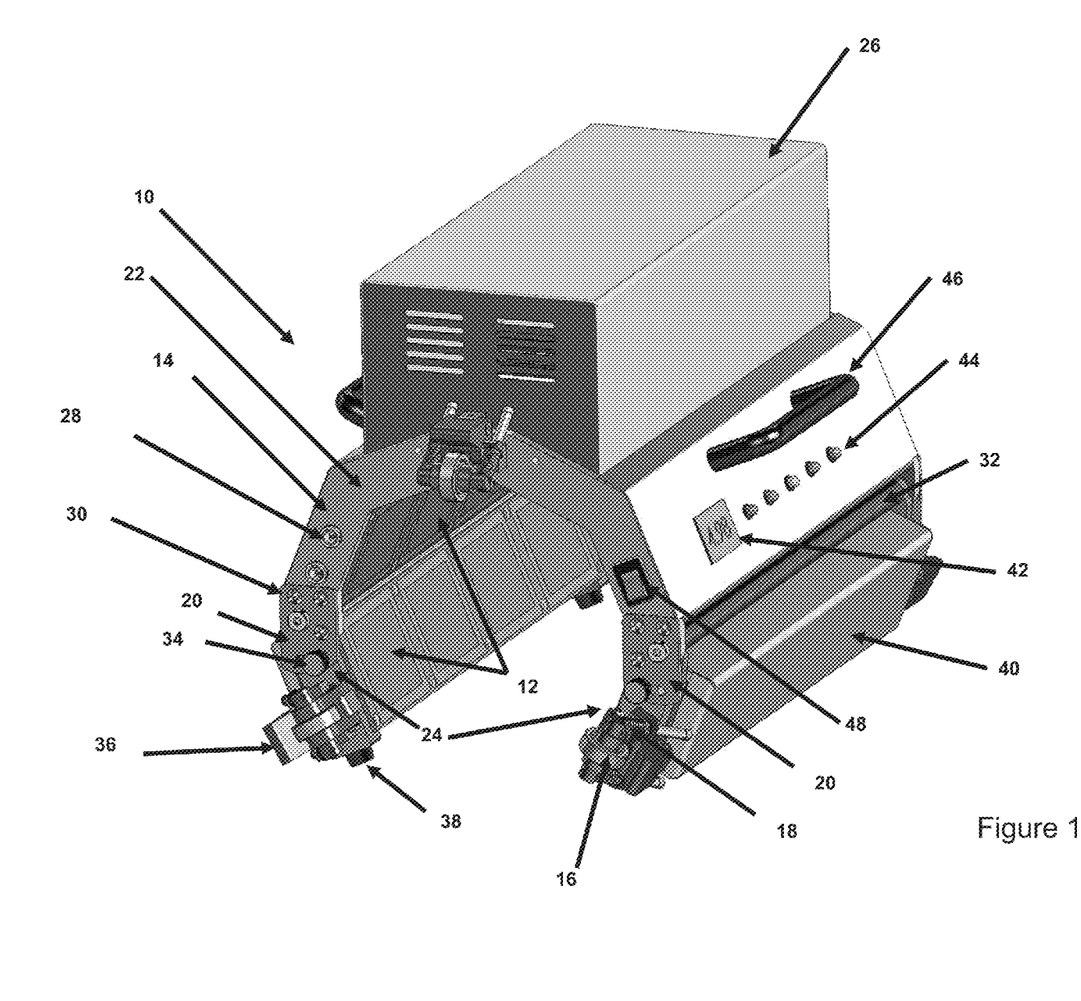
FIG. 1 illustrates one embodiment of the sensor of the present invention.

FIG. 1 illustrates one embodiment of the sensor of the present invention. The sensor 10 consists of an array 12 of capacitive sensor plates that are mounted in a frame 14 that is adapted to wrap substantially around the tendon that is being inspected. In one embodiment, the sensor is comprised of 24 plates.

The frame is preferably equipped with rollers 16 that allow the sensor to roll along the length of the tendon. The rollers are preferably spring loaded 18 and automatically compensate for a specified range of tendon diameters and for diameter variations that are caused by previous repairs to a tendon.

In one embodiment, the frame is in three sections, connected by hinges 20. In the embodiment of FIG. 1, the top section 22 encompasses 180 degrees and two lower sections 24 cover 45 degrees each. There is no bottom segment in this embodiment. This embodiment (not having a bottom section) permits the sensor to work very close to the floor because in many installations there is very little clearance between tendons and floor. An optional bottom section can be attached for close inspection of bottom of the tendon or for shielding the open bottom of the sensor.

A self contained data acquisition system (DAS) 26 acquires signals from the sensor plates and converts the signals into a digital data stream that is transmitted wirelessly to the host computer. The host computer reconstructs 3D images from received signals and views the images in real-time.

A computer board takes the data stream from the DAS, processes the data into a format suitable for transmission and transmits it over a radio link to a host computer for image reconstruction and analysis.

The embodiment of the sensor of FIG. 1 is also comprised of battery charger jacks 28, four latches 30, two hinge pins 32 that run the length of the sensor, thumb screws 34, roller retraction levers 36, rubber feet 38, battery covers 40, battery voltage meter 42, indicator lamps 44 (for indicating status of the DAS including, calibration status, power status, run status, error status, and firmware status for proper firmware loading), carrying handles 46, and a power switch 48. The carrying handles and rubber feet are provided for safe and convenient handling of the sensor.

Figure 2:
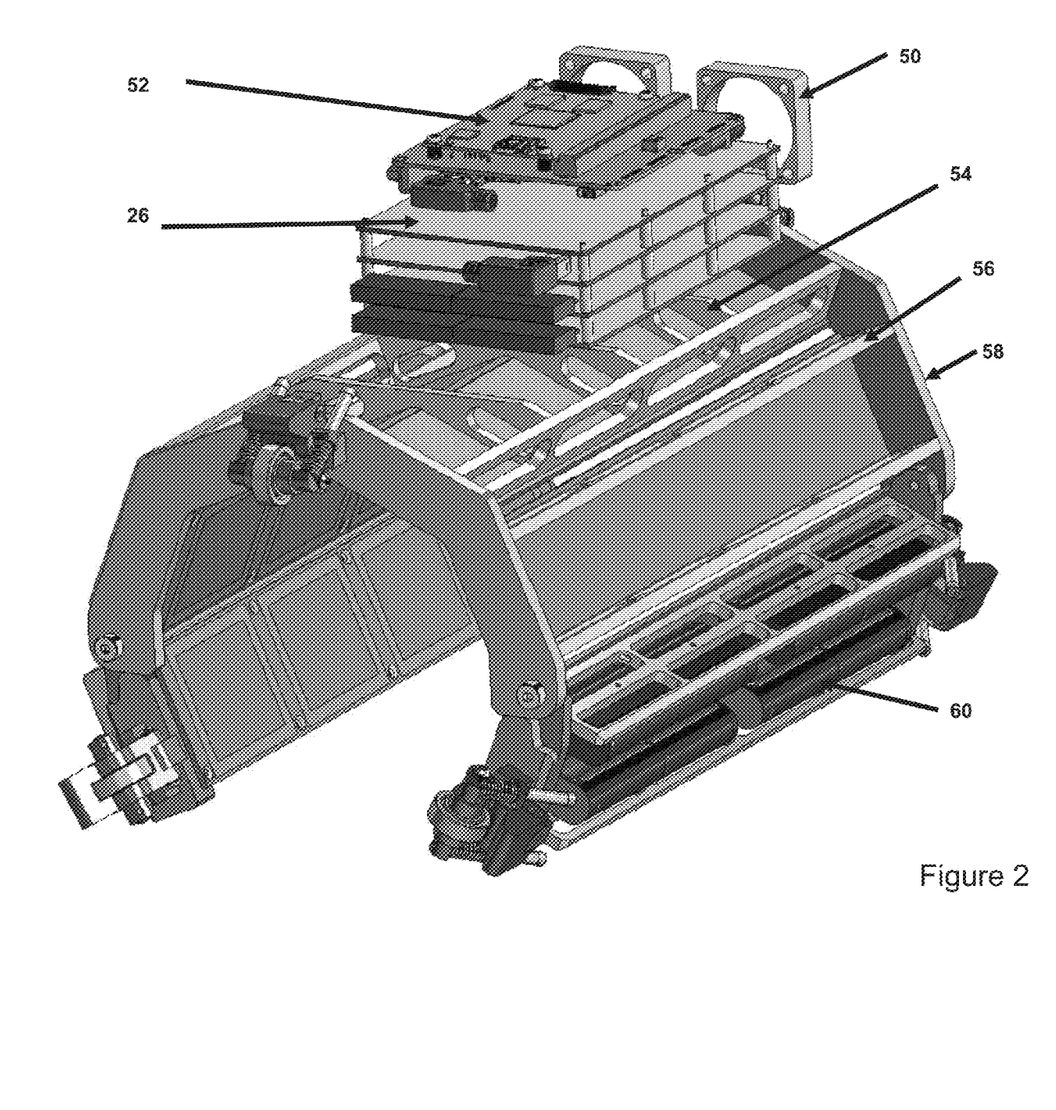
FIG. 2 illustrates the embodiment of the sensor of FIG. 1 in a skeleton view.
Figure 3:
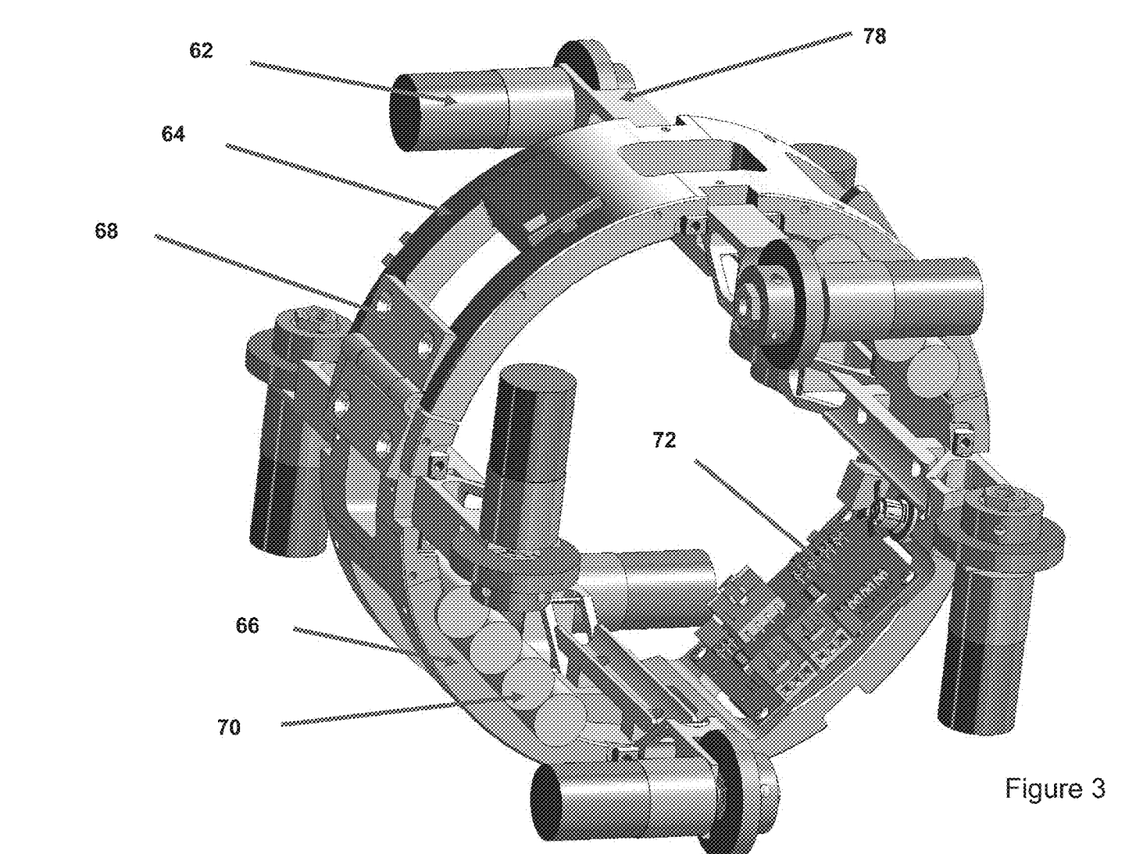
FIG. 3 illustrates one embodiment of the tractor mechanical arrangement. of the present invention.

FIG. 2 illustrates the embodiment of the sensor of FIG. 1 in a skeleton view. This view illustrates the cooling fans 50, computer board 52, roof support beams 54, longitudinal support beams 56, frame end pieces 58, and battery packs 60. An array of rechargeable battery packs provides power for the DAS, the computer board and cooling fans FIG. 3 illustrates one embodiment of the tractor mechanical arrangement. (visible) of the present invention. As illustrated, this embodiment of the tractor mechanical arrangement is comprised of motor-gearheads 62, a short frame portion 64, a long frame portion 66, a hinge 68 connecting the short frame portion to the long frame portion, battery packs 70, motor controller 72, and spring-loaded swing arms 78 (a spring will attach to spring arms of the motors that are on opposite sides of the tractor. A total of 4 springs are preferably used. The springs enable the tractor to adjust for diameter varying tendons while maintaining stability.).

Figure 4:
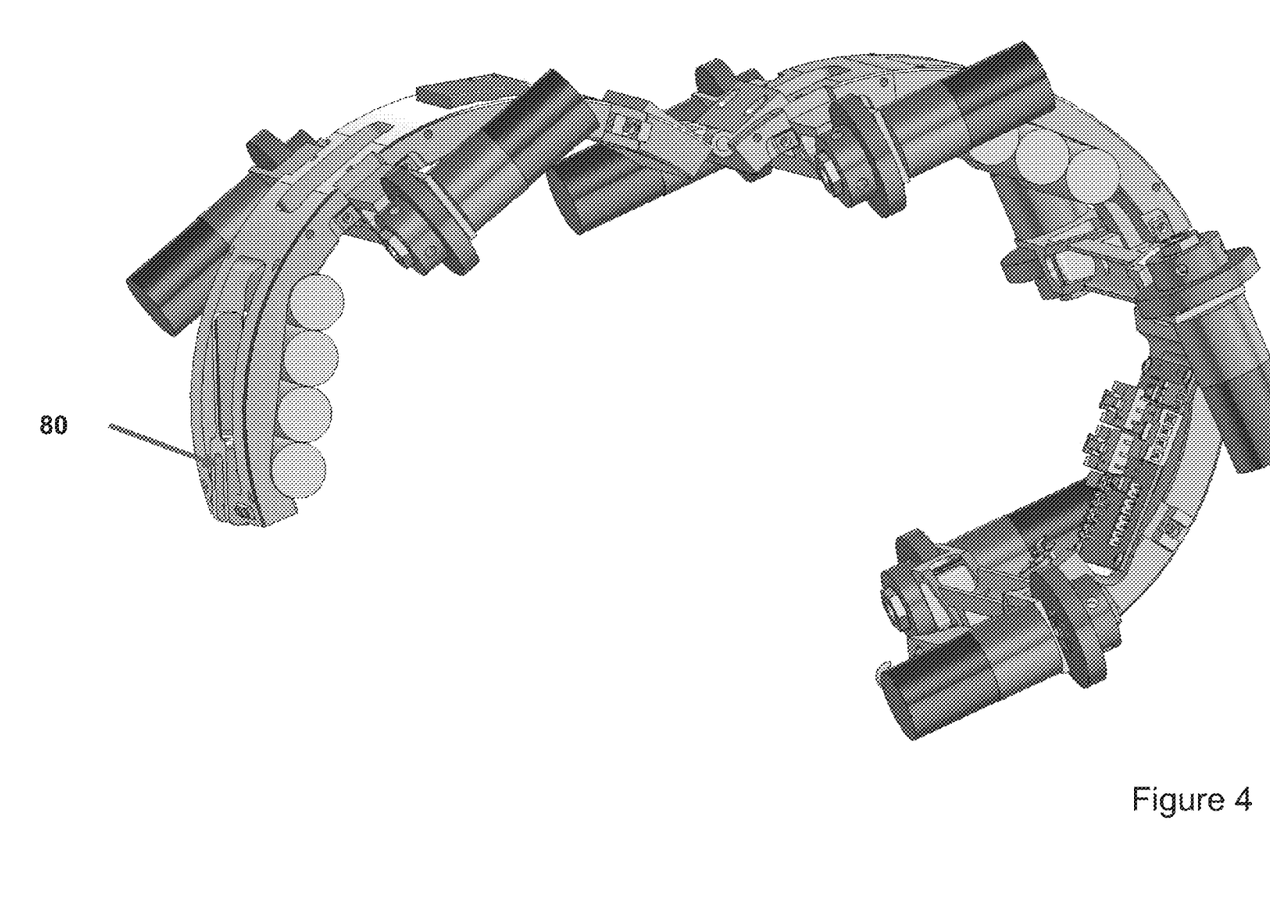
FIG. 4 illustrates one embodiment of the tractor mechanical arrangement of the present invention in an open configuration.

FIG. 4 illustrates one embodiment of the tractor mechanical arrangement of the present invention in an open configuration: The long and short frame portions are hinged open. A latch 80 connects them together when in the closed position. When in a closed position, the tractor arrangement wraps around the structure to be imaged so that the gearheads are positioned on the structure. As the motors turn, the gearheads (being cylindrical in shape) propel the tractor arrangement along the structure. The tractor arrangement, being connected to the sensor, propels the sensor along the structure.

The tractor module of the preferred embodiment has wireless controlled motors to move the sensor along the structure being imaged. For example, for applications that involve cable stays (i.e., long vertical or inclined cables on suspended bridges), it is not feasible for the operator to climb and test those cables using the sensor. Rather, the tractor does this job through a remote control. It also communicates data back to the user computer using a wireless channel. The tractor moves forward, backward, and rotates with remote control commands from the operator (e.g., it rotates by the motors being titled with respect to the axis of the tendon).

In one embodiment, the tractor arrangement connects to the sensor using two extended rods from the tractor and fixed at the sensor. The two rods are preferably 180 degrees from each other. For example, when a tractor arrangement is attached to the sensor, the hinge pins extend and connect to the hinge of the tractor in FIG. 7.

The tractor module arrangement allows the sensor to be self-propelled. The tractor is preferably powered by rechargeable batteries and controlled via a radio link. In one embodiment, the tractor module couples to the sensor using custom designed ball couplers that are easy to connect and disconnect. Tractor wheel rotations can be counted to provide location data of a tendon defect.

Figure 5:
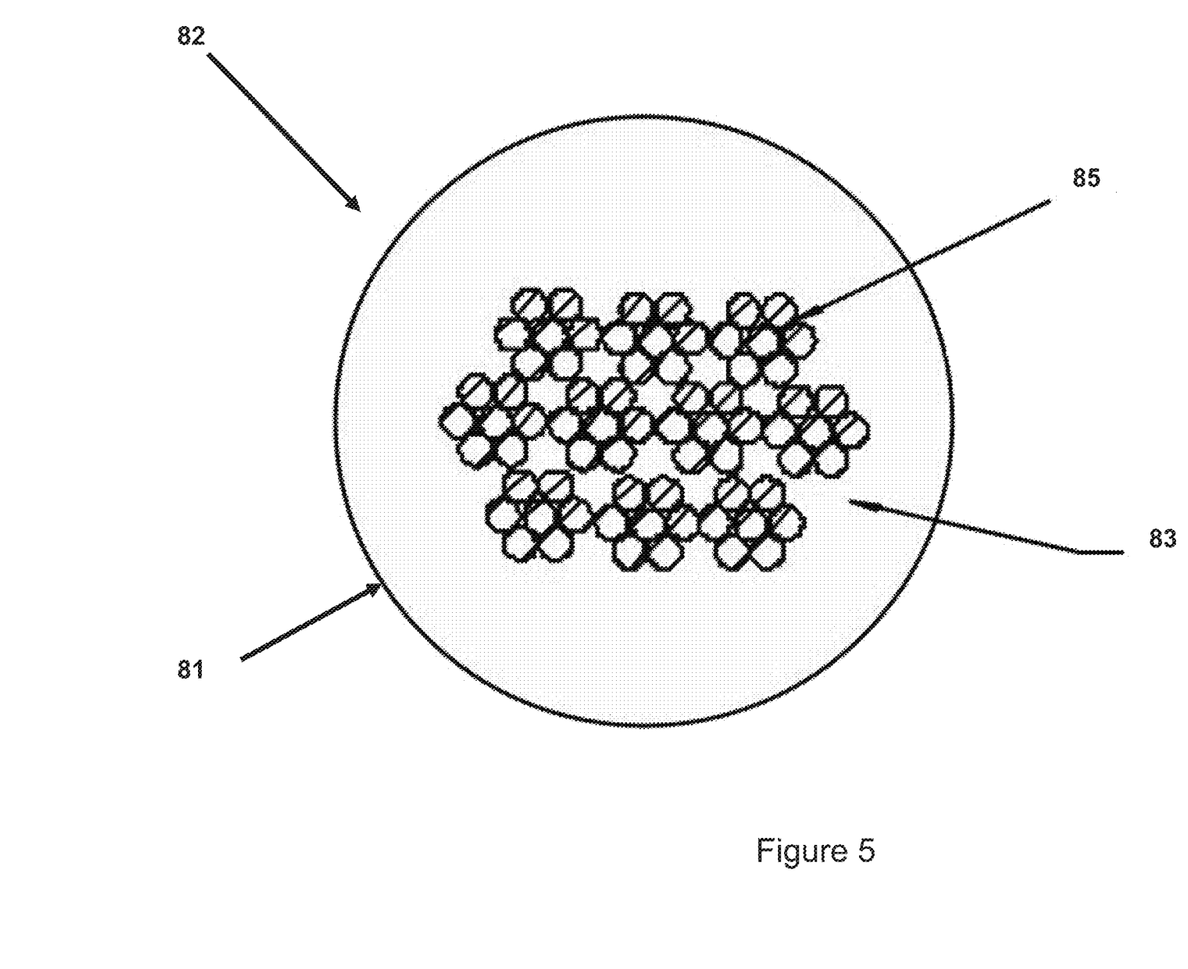
FIG. 5 illustrates a cross-sectional view of an example of a tendon.

FIG. 5 illustrates a cross-sectional view of an example of a tendon 82, e.g., a duct 81, grout 83 and post-tensioned steel system. The steel cables 85 are tensioned, wedge-locked into place and the duct is pumped full of grout which hardens and protects the cables.

Figure 6:
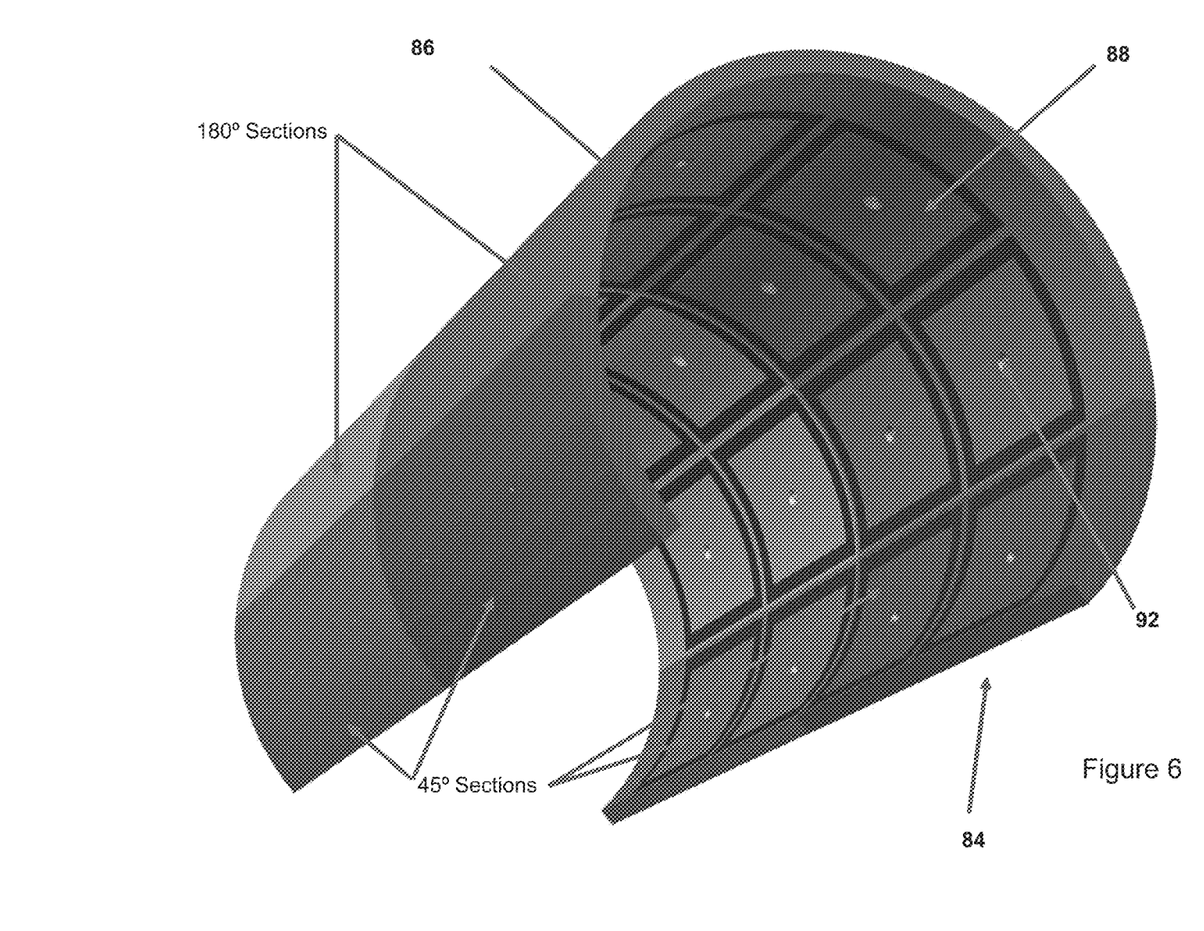
FIG. 6 illustrates one embodiment of an array of sensor plates produced by a 3D printer.

FIG. 6 illustrates one embodiment of an array 84 of sensor plates produced by a 3D printer. This shows an alternative method of producing plates for an ECVT sensor. The plates can be printed in sections to make a large sensor using an economical small bed printer. The 180 degree sections attach to the top section of the sensor of FIG. 1, and the 45 degree sections connect to each of the lower sections, respectively. The array as shown in FIG. 6 is also comprised of a plastic printed substrate 86 (this is the main body of the sensor), gray metallization conductive areas 88 formed by spraying conductive ink or spray or by printing them using conductive filaments (those areas form the plates of the sensor), and countersink holes for electrical contact with screws 92 (those are places where the cable wires are screwed to the conductive plates, thus connecting the plates to the DAS using a coaxial cable without the need for soldering).

Figure 7:
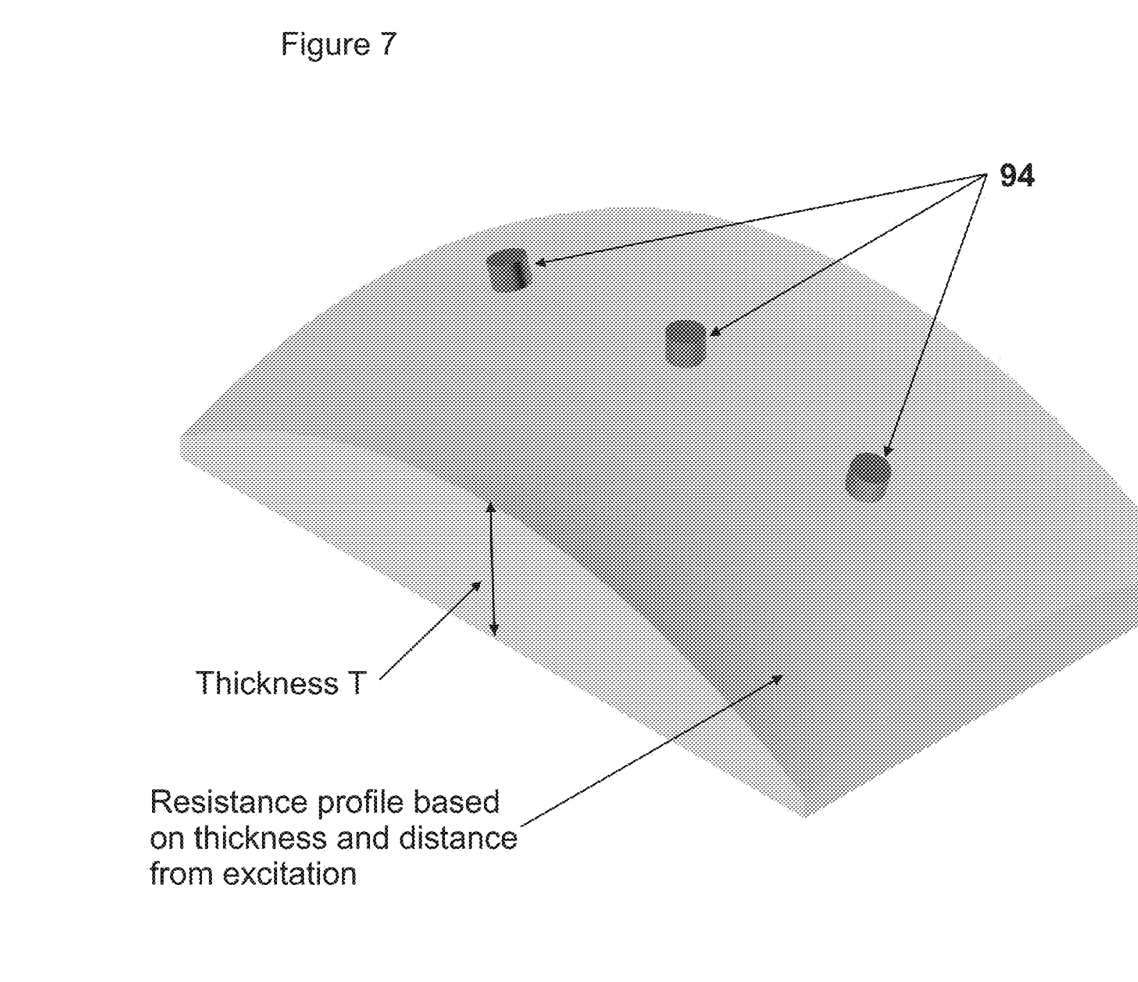
FIG. 7 illustrates an example of resistive distribution using variable thicknesses of resistive material.

FIG. 7 illustrates an example of resistive distribution using variable thicknesses of resistive material. In this example, the plate is a section of a sphere and maximum electric field is produced at the midpoint of the surface, which is the point of maximum conductivity and minimum resistance. The profile can be changed by differential excitation of the different excitation points 94. This is one example and many variations can be produced by changing the shape of the profile of the plate, locations of the excitation points and electrical characteristics of the differential excitation voltages.

Figure 8:
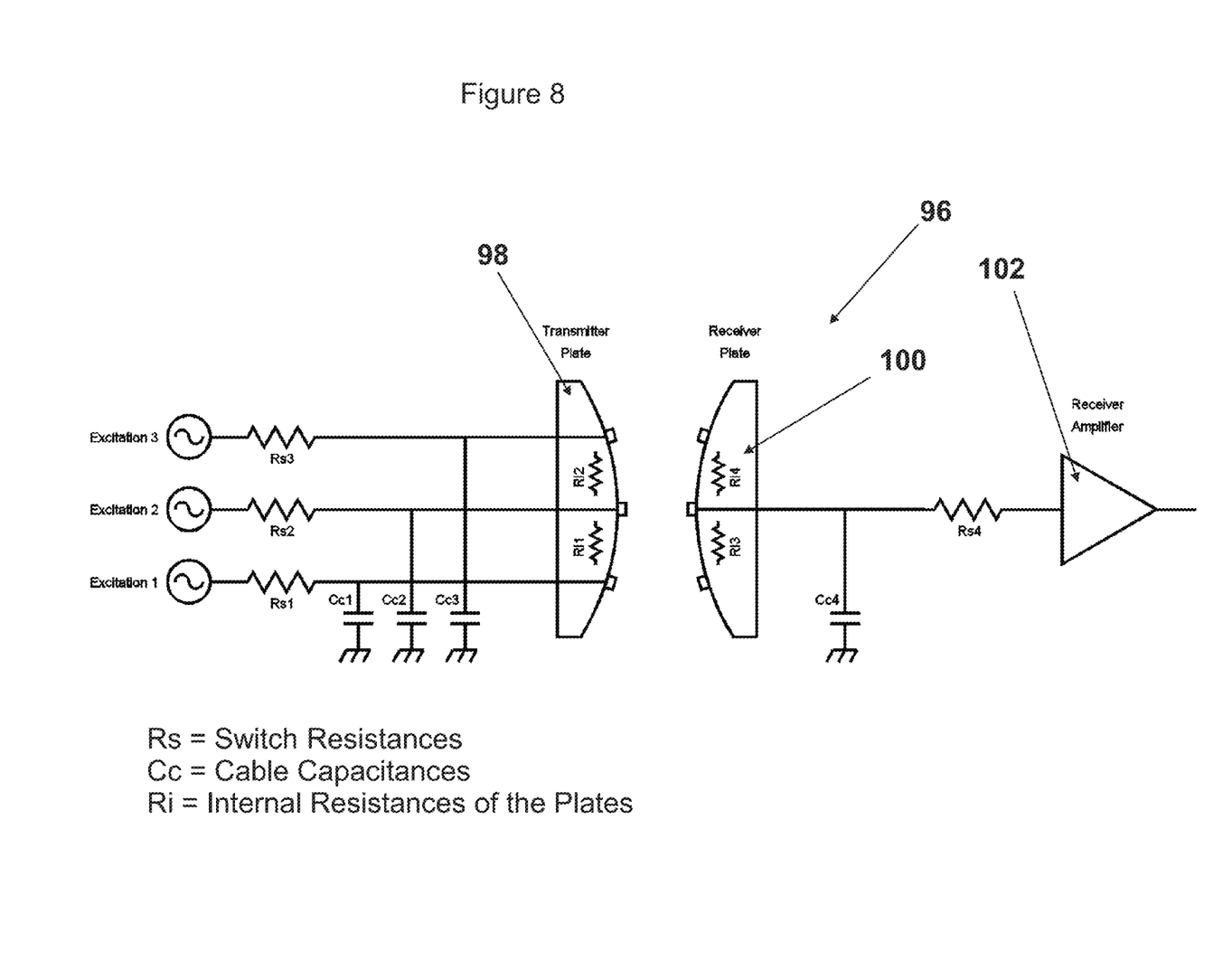
FIG. 8 illustrates an example circuit for providing excitation and receiver signals for one pair of plates of the ECVT sensor.

FIG. 8 illustrates an example circuit 96 for providing excitation and receiver signals for one pair of plates of the ECVT sensor. The transmitter plate 98 can be activated by multiple sources. The receiver plate 100 is preferably connected to a receiver amplifier 102. Switch resistances and cable capacitances are parasitic elements whose effect can be minimized by artful circuit design. Internal resistances of the plates are produced as described previously. This example design can be expanded to include additional excitation sources and additional means of controlling excitation parameters at the transmitter plate. Transmitter and receiver plates are preferably assigned dynamically by switches, so each plate alternately performs as a transmitter or receiver depending on the states of the switches.

The preferred embodiment of the invention uses multiple frequency excitation to detect steel degradation. In general, rusted steel has difference dielectric values at different frequencies. The present invention exploits this feature by measuring the capacitance at difference frequencies. If both measurements are different, this indicates there is rust inside. If both capacitance measurements are very close, this indicates the steel is in good shape. The collective measurements between all plates at different frequencies enables the present invention to identify the volume of rust in a tendon cross-section. This new use of capacitance sensors which can be expanded to steel inspection.

Figure 9:
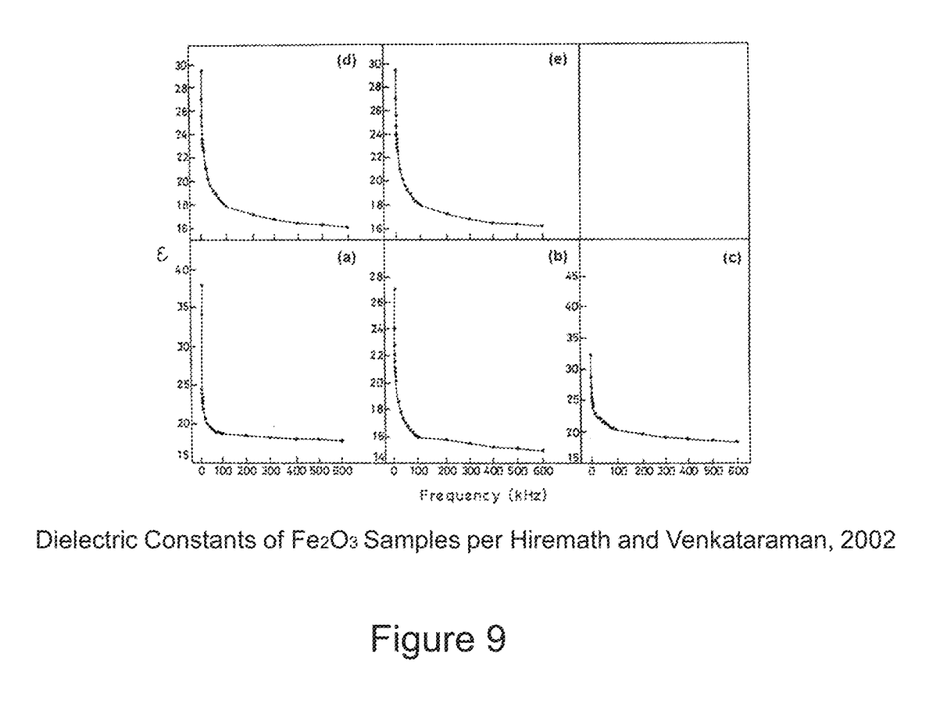
FIG. 9 illustrates the dielectric constant change of steel rust as function of frequency.

FIG. 9 illustrates the dielectric constant change of steel rust as function of frequency. This phenomenon is exploited for imaging and quantifying rust volume by using capacitance tomography sensors, operated at multiple frequencies. The presence of rust on the steel cables or rods inside a tendon can be discriminated by differential imaging with low and high excitation frequencies. The dielectric constant of iron oxide undergoes a sharp reduction at frequencies greater than 100 kHz. This property can be used to distinguish rust from other voids that are filled with water or air. Whereas a tendon with simple air or water voids can be repaired, a tendon with significant amounts of rust would need to be replaced.

Figure 10:
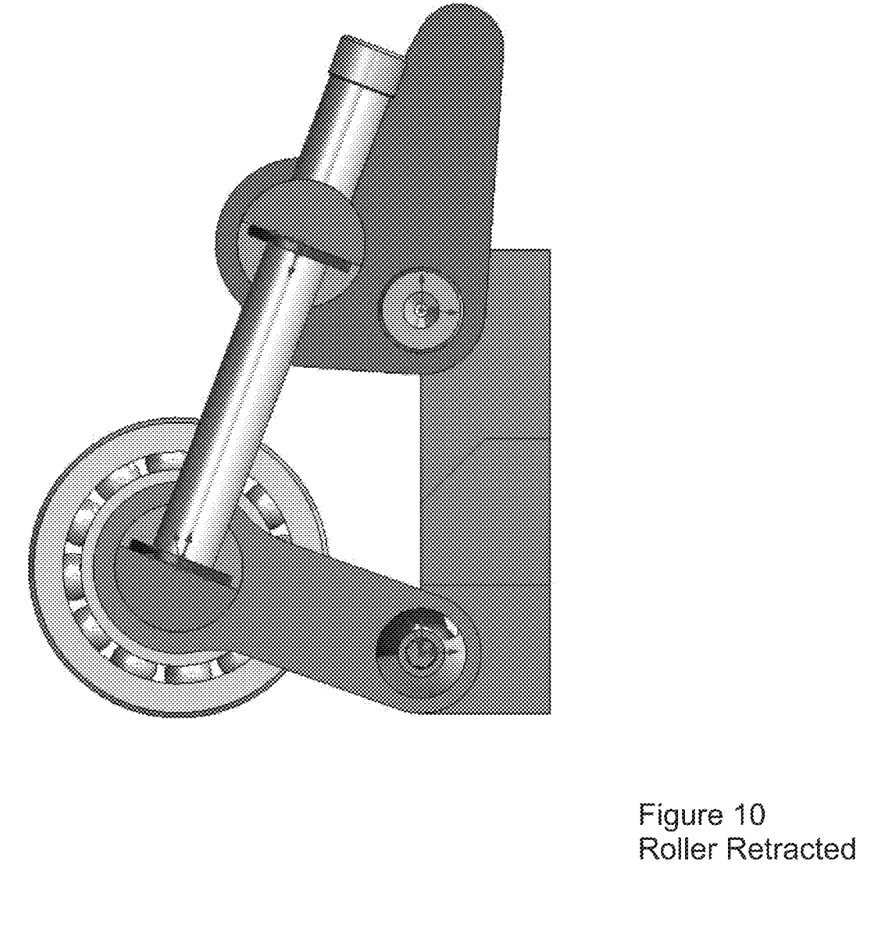
FIG. 10: illustrates one embodiment of the roller retraction lever in position to retract the roller.
Figure 11:
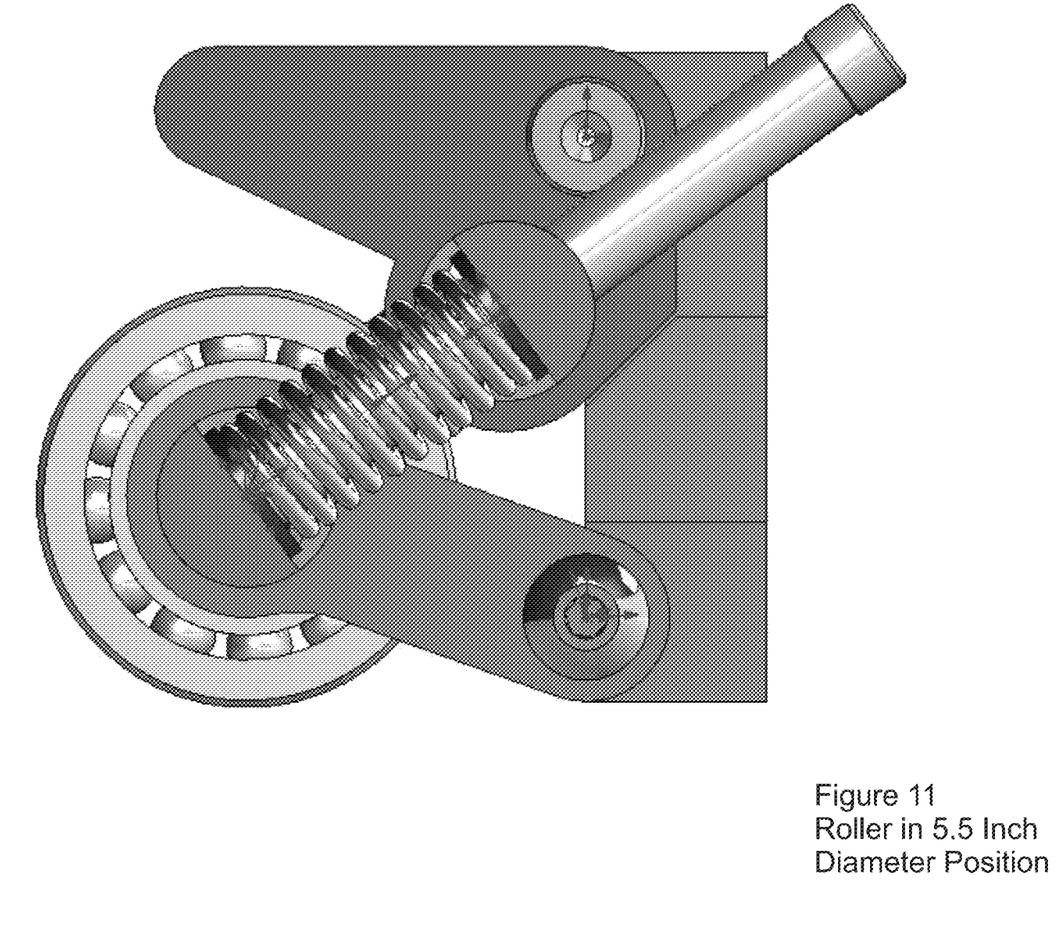
FIG. 11 illustrates the roller retraction lever in position to allow the roller to adjust for the proper operating position.
Figure 12:
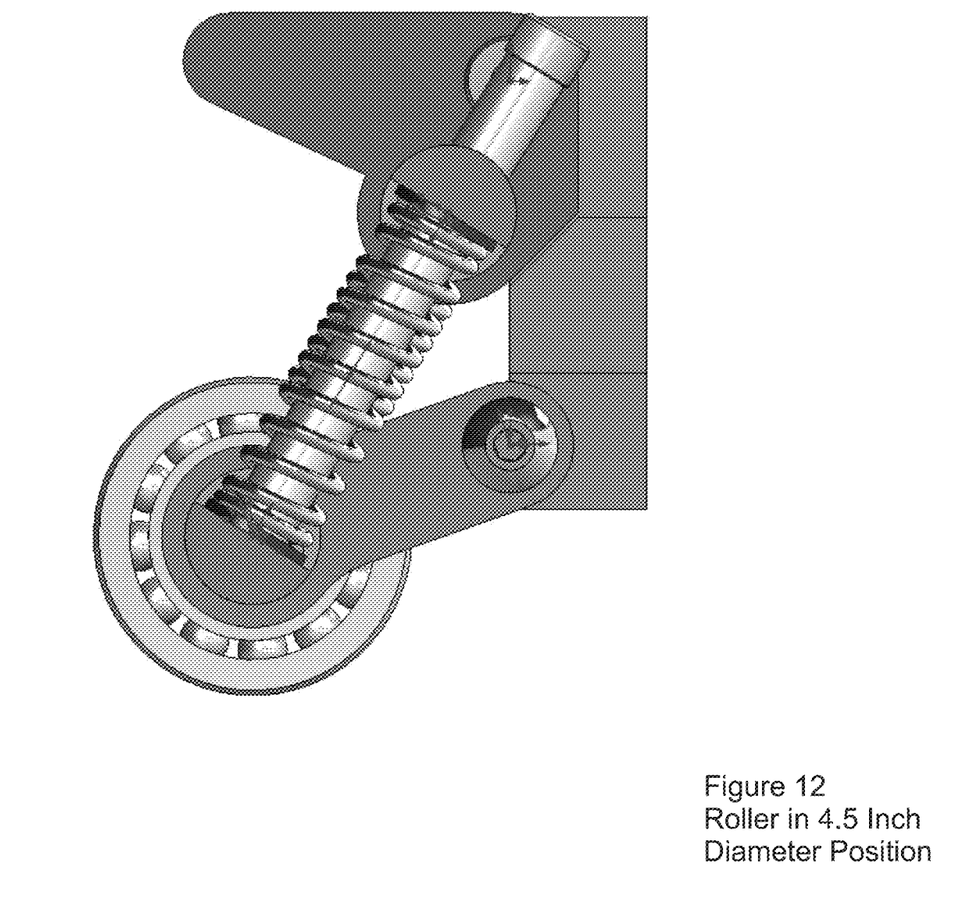
FIG. 12: illustrates the roller retraction lever where the tendon diameter is 4.5 inches.

In a preferred embodiment, the rollers compensate for variation of the tendon diameter. For example, the design range of tendon diameter may be from 4.5 inches to 5.5 inches. As the diameter increases, it pushes the rollers outward, compressing the springs. The spring force is set by design to support the sensor and maintain acceptable position of the image center. FIG. 10: illustrates one embodiment of the roller retraction lever in position to retract the roller. FIG. 11 illustrates the roller retraction lever in position to allow the roller to adjust for the proper operating position. In this figure, tendon diameter is 5.5 inches, causing the springs to compress. FIG. 12: illustrates the roller retraction lever where the tendon diameter is 4.5 inches, allowing the springs to extend to a longer length.

Enhanced imaging resolution can be achieved by steering the electric field produced by each excitation plate (e.g., using AECVT technology). This can be accomplished by a combination of two methods. The first method for steering the field is to produce plates with non-uniform conductivity. This causes the excitation current to be higher in the regions with higher conductivity and vice-versa. Non-uniform plates can be produced on a 3D printer, using a resistive material. Printing thicker areas reduces resistance and increases conductivity, which is the reciprocal, and vice-versa. Non-uniform plates can also be produced by stacking layers of resistive material selectively and fusing them together. The second method for steering the field is to divide each plate into several sub-plates and excite each sub-plate at a different voltage level (AECVT segments). The sub-plates can be different regions within a single non-uniform plate, or the plate can be physically divided. The optimum voltage profile can be estimated from equivalent circuit analysis and measurement of plate to ground capacitance at the transmitter and receiver ends. The profile can be tuned empirically when sub-plate excitation is employed, which allows the profile to be changed by electronic adjustments.

Detection of rust and corrosion of tendon steel is an important consideration for conducting effective inspections. The dielectric constant of iron oxide (rust) is not constant and is influenced by the frequency at which it is measured. Taking advantage of the frequency synthesizer that generates the excitation voltage in the data acquisition system, imaging can be accomplished using different excitation frequencies. The presence of rust can be inferred from the differential measurements. Rust and corrosion of steel reduce the percentage of pure metal in the tendon. The effect of pure metal rods or strands in the tendon increases effective capacitance because they steer the electric field between the transmitter and receiver plates. Therefore, rusted or corroded rods or strands have a reduced effect and this shows up as a variation in measured capacitance as the sensor travels along the tendon.

In one example of applying the sensor of the present invention, a user will acquire drawings of the tendon system, develop a testing plan, and clear debris from the tendons to be inspected. The user should also identify and record previously repaired sections. The next step is to calibrate the sensor on a test tendon that has known locations of a void, a water pocket and a bleeding grout pocket. Reference images should be obtained that show the defects and broken steel strands within the test tendon.

The sensor is then mounted on the tendon to be inspected and testing should be conducted to assure that it rolls properly. Data acquisition processes are initiated and inspection is performed using manual propulsion of the sensor.

If the tractor module is needed, it can be mounted to the tendon or cable stay and coupled it to the sensor. If a discontinuity is observed, the tractor can be stopped, put in reverse, and the sensor can identify the location by driving the tractor forward and backward until the defect is precisely located. The image can be examined to determine the nature and size of the defect and note if there are broken steel strands or evidence of steel loss due to corrosion.

While certain embodiments of the present invention are described in detail above, the scope of the invention is not to be considered limited by such disclosure, and modifications are possible without departing from the spirit of the invention as evidenced by the following claims

What is claimed is:

1. A sensor for providing three-dimensional tomography of the interior of tendons, cable-stays and other similar structures, comprising:
   a frame adapted to open and close, wherein the frame is adapted to wrap around the tendon, cable-stay or other similar structure when in a closed position;
   a plurality of sensor plates supported in place by the frame, and wherein the plurality of sensor plates wrap around the tendon, cable-stay or other similar structure when the frame is in a closed position, and wherein the sensor is adapted to provide sensitivity in three geometric dimensions;

wherein the sensor is an electrical capacitance volume tomography sensor and wherein each of the plurality of sensor plates are capacitance plates;

a plurality of roller assemblies or skids supported by the frame for facilitating movement of the sensor on the tendon, cable-stay, or other similar structure;

data acquisition electronics in communication with the plurality of sensor plates for receiving input data relating to capacitance data from the plurality of sensor plates; and wherein the sensor is adapted to provide multi-frequency excitation of the plurality of capacitance plates for detecting steel degradation in the tendon, cable-stay, or other similar structure.

2. A sensor according to claim 1, further comprising:
a processing system in communication with the data acquisition electronics, the processing system programmed with instructions for executing on the processing system to reconstruct a three-dimensional volume-image from the input data collected from the data acquisition electronics.

3. A sensor according to claim 2, further comprising:
a radio link for transmission of sensor data to the processing system for image reconstruction and analysis.

4. A sensor according to claim 1, wherein the sensor is an adaptive electrical capacitance volume tomography sensor and wherein each of the plurality of capacitance plates are comprised of a plurality of segments that are individually addressable by voltages and where sensor sensitivity can be controlled by varying the voltage distribution or envelope applied to the capacitance plate segments.

5. A sensor according to claim 1, wherein the sensor is connected to a motor-driven module for providing movement to the sensor, further comprising at least one motor, a motor controller adapted to for wireless control of the motor, a module frame for supporting the motor, and wherein the module frame is adapted to wrap around the tendon, cable-stay, or other similar structure when the module frame is in the closed position.

6. A sensor according to claim 1, wherein the frame is comprised of three sections hinged together.

7. A sensor according to claim 1, wherein the roller assemblies each have a self-adjusting extension to accommodate a range of tendon diameters.

8. A sensor according to claim 1, wherein the roller assemblies are comprised of discrete rollers, captive balls, or bearings.

9. A sensor according to claim 5 wherein the motor-driven module is adapted for modular attachment with the sensor and is capable of autonomous travel.

10. A sensor according to claim 1 wherein the frame does not completely wrap around the tendon, cable-stay or other similar structure for allowing the sensor to work close to the floor on low mounted structures.

11. A sensor according to claim 1, wherein the plurality of sensor plates form an array formed using a 3D printer and having a conductive coating, wherein each plate is further comprised of isolated regions printed with removable material that can be dissolved or chipped out.

12. A sensor according to claim 1 wherein the plurality of sensor plates form an array formed with plates having a variable resistive profile to establish voltage gradients on the plates to improve capacitance measurements.

13. A sensor according to claim 12, wherein variability is introduced into the sensor by varying plate thickness or by layering of plate materials.

14. A sensor for providing three-dimensional tomography of the interior of tendons, cable-stays and other similar structures, comprising:
a frame adapted to open and close, wherein the frame is adapted to wrap around the tendon, cable-stay or other similar structure when in a closed position;
a plurality of sensor plates supported in place by the frame, and wherein the plurality of sensor plates wrap around the tendon, cable-stay or other similar structure when the frame is in a closed position, and wherein the sensor is adapted to provide sensor sensitivity in three geometric dimensions;
a plurality of roller assemblies or skids supported by the frame for facilitating movement of the sensor on the tendon, cable-stay, or other similar structure;
data acquisition electronics in communication with the plurality of sensor plates for receiving input data from the plurality of sensor plates;
wherein the sensor is adapted to provide multi-frequency excitation of the plurality of sensor plates;
a processing system in communication with the data acquisition electronics, the processing system programmed with instructions for executing on the processing system to: 1) reconstruct a three-dimensional volume-image from the input data collected from the data acquisition electronics; 2) determine whether there is steel degradation in the tendon, cable-stay, or other similar structure by processing the input data received from the data acquisition electronics from excitation of the sensor plates at multiple frequencies; and 3) determine whether there are air pockets, water pockets, or bleeding-grout pockets in the tendon, cable-stay, or other similar structure by processing the input data received from the data acquisition electronics.

15. A sensor according to claim 14, wherein the processing system is programmed with instructions for executing on the processing system to collect capacitance using a first frequency, to collect capacitance at a second frequency, and to use the difference between both measured capacitances to image the location and volume of steel rust.

16. A sensor according to claim 14, wherein the sensor is connected to a motor-driven module for providing movement to the sensor, further comprising at least one motor, a motor controller adapted to for wireless control of the motor, a module frame for supporting the motor, and wherein the module frame is adapted to wrap around the tendon, cable-stay, or other similar structure when the module frame is in the closed position.

17. A method for providing three-dimensional tomography of the interior of tendons, cable-stays and other similar structures, comprising the steps of:
providing a sensor having:
a frame adapted to open and close, wherein the frame is adapted to wrap around the tendon, cable-stay or other similar structure when in a closed position;
a plurality of sensor plates supported in place by the frame, and wherein the plurality of sensor plates wrap around the tendon, cable-stay or other similar structure when the frame is in a closed position, and wherein the sensor is adapted to provide sensor sensitivity in three geometric dimensions;
a plurality of roller assemblies or skids supported by the frame for facilitating movement of the sensor on the tendon, cable-stay, or other similar structure;
a data acquisition electronics in communication with the plurality of sensor plates for receiving input data from the plurality of sensor plates;

moving the sensor along the tendon, cable-stay, or other similar structure;
providing multi-frequency excitation of the plurality of sensor plates for detecting steel degradation in the tendon, cable-stay, or other similar structure;
reconstructing a three-dimensional volume-image from the input data collected from the data acquisition electronics;
collecting capacitance using a first frequency;
collecting capacitance at a second frequency, and using the difference between both measured capacitances to image the location and volume of steel rust;
determining whether there is steel degradation in the tendon, cable-stay, or other similar structure by processing the input data received from the data acquisition electronics from excitation of the sensor plates at multiple frequencies.

18. A method according to claim 17 wherein the other similar structure is a pipeline.

19. A sensor for providing three-dimensional tomography of the interior of tendons, cable-stays and other similar structures, comprising:
a frame adapted to open and close, wherein the frame is adapted to wrap around the tendon, cable-stay or other similar structure when in a closed position;
a plurality of sensor plates supported in place by the frame, and wherein the plurality of sensor plates wrap around the tendon, cable-stay or other similar structure when the frame is in a closed position, and wherein the sensor is adapted to provide sensitivity in three geometric dimensions;
a plurality of roller assemblies or skids supported by the frame for facilitating movement of the sensor on the tendon, cable-stay, or other similar structure;
data acquisition electronics in communication with the plurality of sensor plates for receiving input data from the plurality of sensor plates; and
wherein the sensor is adapted to provide multi-frequency excitation of the plurality of sensor plates for detecting steel degradation in the tendon, cable-stay, or other similar structure;
wherein the processing system is programmed with instructions for executing on a processing system to: 1) determine whether there is steel degradation in the tendon, cable-stay, or other similar structure by processing the input data received from the data acquisition electronics from excitation of the sensor plates at multiple frequencies; and 2) determine whether there are air pockets, water pockets, or bleeding-grout pockets in the tendon, cable-stay, or other similar structure by processing the input data received from the data acquisition electronics;
and
wherein the processing system is programmed with instructions for executing on the processing system to collect capacitance using a first frequency, to collect capacitance at a second frequency, and to use the difference between both measured capacitances to image the location and volume of steel rust.

\* \* \* \* \*